United States Patent [19]

De Bold

[11] Patent Number: 4,647,455
[45] Date of Patent: Mar. 3, 1987

[54] PROCESS FOR EXTRACTING ATRIAL NATRIURETIC FACTOR

[75] Inventor: Adolfo J. De Bold, Kingston, Canada

[73] Assignee: Queen's University at Kingston, Canada

[21] Appl. No.: 683,311

[22] Filed: Dec. 18, 1984

Related U.S. Application Data

[63] Continuation of Ser. No. 473,442, Mar. 9, 1983, abandoned, which is a continuation-in-part of Ser. No. 351,036, Feb. 22, 1982, abandoned.

[30] Foreign Application Priority Data

Feb. 21, 1983 [CA] Canada ................................. 421998

[51] Int. Cl.$^4$ ...................... A61K 35/34; C07K 1/14; C07K 15/06
[52] U.S. Cl. ...................................... 424/95; 514/21; 514/869; 530/425
[58] Field of Search ..................... 424/177, 95; 514/21; 530/425

[56] References Cited

U.S. PATENT DOCUMENTS 3,822,348   7/1974   Higashi et al. ....................... 424/95

OTHER PUBLICATIONS

Bennett et al, Biochemistry 1981 20, 4530–4538.
deBold et al., J. Histochem. Cytochem. 1978, vol. 26, No. 12, pp. 1094–1102.
DeBold et al., Life Sciences vol. 28(1), 89–94, 1981 via Chem. Abstracts vol. 94 62919(f).
de Bold, Canadian Journal of Physiology and Pharmacology, vol. 60, No. 3, pp. 324–330 (1982).
Abstract No. 1846, Part 1 of 65th Annual Meeting of Federation of American Society for Experimental Biology, Atlanta, GA, Apr. 12–17, 1981.
Abstract Published Mar. 1, 1981, cited by Trippodo et al, as de Bold, Fed. Proc., vol. 40, p. 554 (Abstract), 1981.
Trippodo et al, Proceedings of the Society for Experimental Biology and Medicine, vol. 170, pp. 502–508, 1982.

*Primary Examiner*—Alan Siegel
*Assistant Examiner*—Jacqueline M. Stone
*Attorney, Agent, or Firm*—Lowe, Price, Leblanc, Becker & Shur

[57] ABSTRACT

Diuretic and natriuretic extracts, at least partially characterized as peptides, have been obtained by homogenization of mammalian heart atria with an aqueous solution of a lower carboxylic acid. After precipitation of impurities by pH adjustment, the extract may be further purified chromatographically. Extracts injected into text rats resulted in 30–40 fold increases in sodium and chloride excretions within 5–10 minutes of injection. Urine volume rose 10–15 fold and potassium excretion doubled. The response was complete in 20 minutes and no similar changes in renal function were observed following injection of a similarly obtained ventricular extract.

2 Claims, 11 Drawing Figures

PROCESS FOR EXTRACTING ATRIAL NATRIURETIC FACTOR

This application is a continuation of application Ser. No. 473,442, filed Mar. 9, 1983, abandoned, which is a continuation-in-part of Ser. No. 351,036, filed Feb. 22, 1982, now abandoned.

OBJECT OF THE INVENTION

This invention relates to diuretic and natriuretic factor and a process for extraction thereof from mammalian heart atria, especially rat hearts.

BACKGROUND OF THE INVENTION

It is known that the muscle cells of the atrial myocardium in mammals contain, in addition to contractile elements similar to those found in ventricular fibers, a highly developed Golgi complex, a relatively high proportion of rough endoplasmic reticulum, and numerous membrane bound storage granules, referred to as specific atrial granules. No such granules appear to exist in ventricular muscle cells. Morphologically and histochemically the atrial granules resemble those present in polypeptide-hormone producing cells (J. Histochem. Cytochem. 26, 1094–1102 (1978) de Bold et al). It is also known (Life Sciences, Vol. 28 pp 89–94 (1981) de Bold et al) that injection of a crude extract of rat atrial myocardium induces a very potent and immediate natriuretic response in non-diuretic assay rats. The problem remains, however, to isolate and identify the atrial natriuretic factor (ANF) contained in the crude extract of the specific atrial granules.

STATEMENT OF INVENTION

It is, therefore, an object of the present invention to provide a process for the extraction of ANF from mammalian heart atria.

It is another object of the invention to provide an extract from mammalian heart atria having diuretic and natriuretic activity.

Thus, by one aspect of the invention there is provided a process for extracting a diuretic and natriuretic factor from mammalian heart atria comprising:

(a) homogenizing mammalian heart atria in an aqueous solution containing a lower carboxylic acid to thereby extract said factor into said solution;

(b) adjusting the pH of said solution within the range 4.5 to 7.6 to thereby precipitate impurities therefrom; and (c) chromatographically purifying said natriuretic factor remaining in said solution.

By another aspect of the invention there is provided a diuretic and natriuretic peptide composition obtained by carboxylic acid extraction from mammalian heart atria.

DESCRIPTION OF DRAWINGS

The invention will be described in more detail hereinafter with reference to the following drawings in which.

DETAILED DESCRIPTION OF PREFERRED EMBODIMENTS

Figure 1:
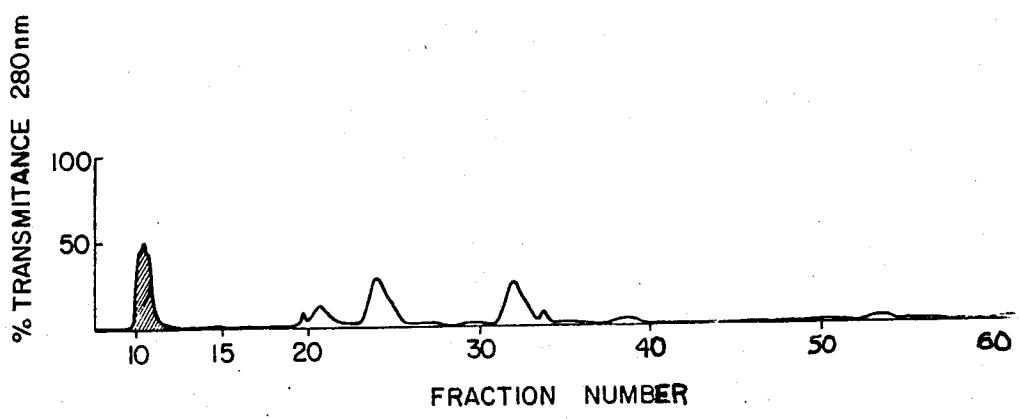
FIG. 1 is a graph illustrating chromatographic desalting of rat atrial extract in Bio-Gel ® P-2. Sample size: 10 ml of acetic acid extract obtained from 5 g of tissue. Column size: 2.6×60 cm. Fraction Size: 11 ml. Eluant: 1.0M acetic acid. Linear flow rate: 2 cm/h. Hatched area indicates fractions where natriuretic activity is recovered.

The presence of secretory-like specific atrial granules in cardiac atrial muscle fibers which has been recognized for some years (J. Cell. Biol. 23, 151 (1964) Jamieson et al) and the more recent finding that crude rat heart atrial muscle extracts are able to induce a very potent diuretic and natriuretic response in assay rats (Life Sciences 28, 89, (1981) de Bold et al) is believed to be of considerable importance to studies for in-vivo water and electrolyte balance. The problem remains however that the crude extract heretofore produced is not sufficiently purified to make a positive identification of the active factor. While a simple homogenization of heart tissue in water or buffered solutions may be employed for extraction of ANF, such a procedure is relatively slow and the concentration of the resulting ANF is very low. Upgrading is tedious and costly. Somewhat surprisingly, although extractions from large mammalian hearts, such as beef, can be effected the natriuretic factor therein appears to be but a very minor component even in the active U.V.-absorbing material isolated after ion exchange chromatography and the total extractable activity appears to be much lower than that obtained from an equivalent amount of rat tissue. Rat atria are therefore the preferred source material.

It has now been determined that advantage may be taken of the well known peptide-solvent properties of lower carboxylic acids such as formic and acetic acid etc., and two alternative techniques will be described in more detail hereinafter. In both techniques, rat atria provided the source material. In the first technique use is made of the extractive properties of 1.0M acetic or other lower carboxylic acid optionally containing protease inhibitors. Following extraction, some contaminants are eliminated by precipitation after adjusting the pH to a range between about 4.5 to about 7.6. The volume of the extract is then reduced, preferably by freeze drying and further purified by gel chromatography and ion exchange chromatography.

EXAMPLE 1

Atria were obtained from male Sprague-Dawley rats (300–350 g). Up to 100 atria (10 g wet weight) were used in each experiment. The animals had free access to food and water until sacrificed by decapitation. The hearts were rapidly removed and placed in ice cold phosphate buffered saline (PBS: 0.9% NaCl in 5 mM sodium phosphate buffer, pH 7.2). The atria were dissected, thoroughly rinsed in PBS, blotted dry and weighed. Ventricular tissues were similarly treated to provide controls. Five volumes of cold 1.0M acetic acid, containing 1 mg of the protease inhibitors pepstatin A and phenylmethylsulfomyl fluoride, were added per gram of tissue wet weight. The tissue was then homogenized in a Polytron ®, let to stand for 1 h on ice and centrifuged at 4° C. for 30 min at 10,000 g. The supernatant from this centrifugation was saved and the pellet re-homogenized in 2.5 volumes of acetic acid and treated as above. The combined supernatant from the two acetic acid extractions was then adjusted to pH 7.6 and centrifuged once again. The supernatant from this centrifugation was freeze-dried, resuspended in 1.0M acetic acid and desalted at 4° C. in a Bio-Gel ® P-2 column (2.6×60 cm) equilibrated with 1.0M acetic acid. The void volume from this column was freeze-dried, resuspended in 1.0M acetic acid and applied to a Sephadex ® G-75 column (2.6×90 cm) equilibrated with 1.0M acetic acid. Pooled active fractions obtained after this chromatography were freeze-dried. The product obtained is referred to as "partially purified natriuretic factor.

EXAMPLE 2

To study the effect of protease (Pronase) on partially purified natriuretic factor, dilutions were made in 0.05M TRIS buffer, pH 7.6. Digestions were carried out by incubating 50 µg of partially purified natriuretic factor with 0.1 U of Pronase for 4 h at 37° C. in a total volume of 1.1 ml of 0.05M TRIS buffer, pH 7.6. The reaction was terminated by addition of 0.2 ml of glacial acetic acid and cooled on ice. After freeze-drying, the samples were resuspended in 1.0 ml of PBS, centrifuged, and 0.2 ml aliquots tested for natriuretic activity.

Further purification of natriuretic factor was accomplished by ion exchange chromatography in CM Bio-Gel ® equilibrated with 0.1M ammonium acetate buffer, pH 4.7. Column size was 0.9×12 cm. Elution was carried out with 13 column volumes under starting conditions followed by a 13 column volumes gradient to 0.1M ammonium acetate, pH 7.0 and, finally, with 13 column volumes from 0.1M ammonium acetate, pH 7.0 to 0.5M ammonium acetate, pH 7.0.

EXAMPLE 3

Natriuretic factor assays were carried out in non-diuretic rats as follows:

Male Sprague-Dawley rats (wt. range 250–372 g) were anaesthetized (Inactin ®, 10 mg/100 g body wt. i.p.) and prepared for bioassay. Arterial blood pressure and heart rate were measured through a femoral artery cannula. A bladder catheter allowed quantitative collection of urine, and a femoral vein cannula was used for maintenance infusion and injection of test material. On completion of surgery a priming dose of Ringer's solution (1.2 ml) containing $^3$H inulin (4.0 µCi/ml) was administered over 20 min, followed by constant infusion of the same solution throughout the experiment at 1.2 ml/hr. The animals were let to stabilize for a further 20 min. During the following 20 min urine was quantitatively collected (control period) after which injection of 0.2 ml of the test sample was made over approximately 5 s. Urine was then collected for the next 20 min (test period). A photoelectric drop counter was positioned between the bladder catheter and the collection tube to qualitatively assess the diuretic response. Urine sodium and potassium concentrations were measured by flame photometry, chloride by electrometric titration and urine volumes by weighing. Protein estimation was made by measuring absorbance at 280 nm (10 mm path) assuming 1 AU-1 mg protein/ml. Statistical comparisons were carried out using unpaired student's t-test.

RESULTS

Figure 2:
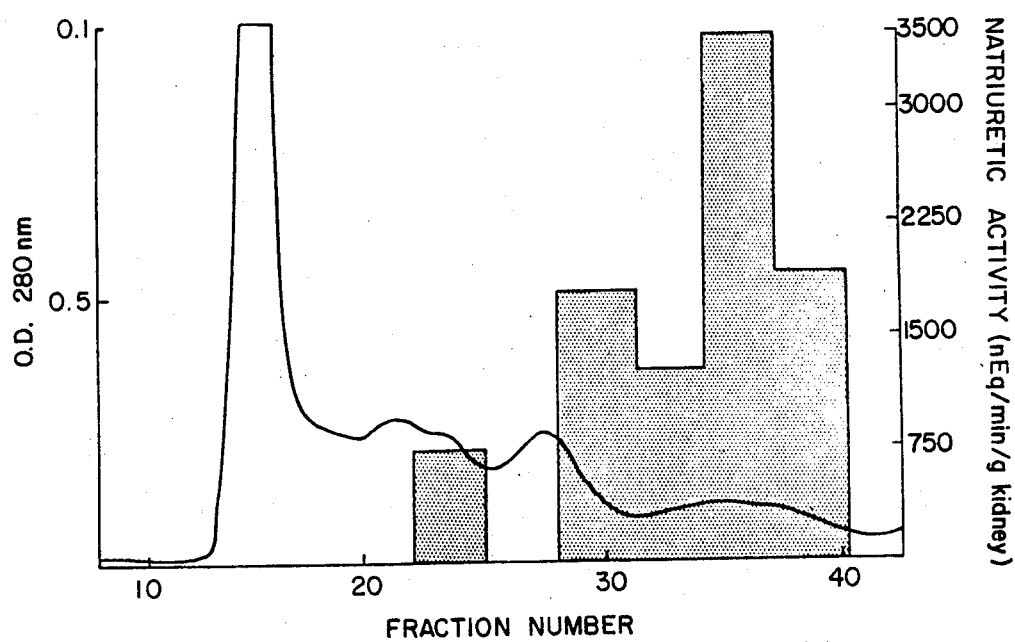
FIG. 2 is a graph illustrating chromatography of rat atrial extract (after desalting in Bio-Gel ® P-2) in Sephadex ® G-75. Column size 2.6×90 cm. Fraction size 11 ml. Eluant: 1.0M acetic acid. Linear flow rate: 5 cm/h. Natriuretic activity (bars) was determined by injecting freeze-dried aliquots of pooled fractions resuspended in PBS.
Figure 3:
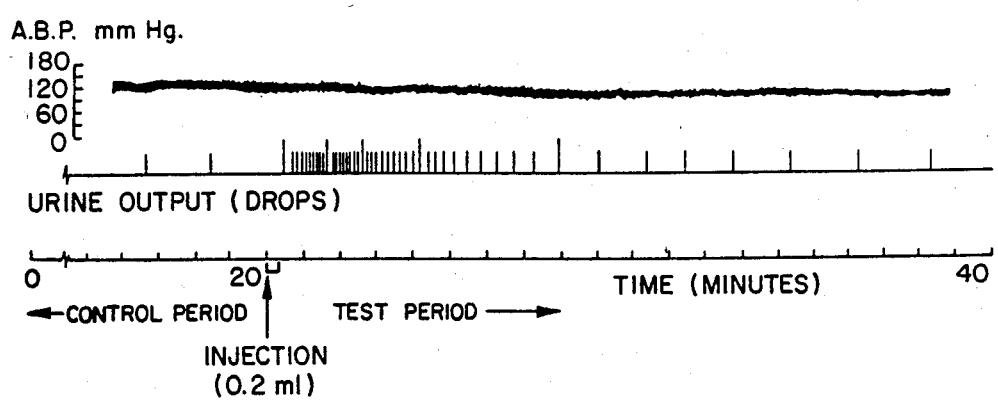
FIG. 3 is a bar graph illustrating typical effect of an injection of partially purified rat atrial natriuretic factor on arterial blood pressure and urine output (in drops) of bioassay rats.

Pooled active freeze-dried fractions, obtained after chromatographic desalting in Bio-Gel ® P-2 (FIG. 1) or after fractionation in Sephadex ® G-75 (FIG. 2), and injected dissolved in PBS, induced a typical response in assay rats (FIG. 3). In terms of urine output, this response was characterized by rapid onset (1–2 min) and decay (10–15 min). By the end of the test period—i.e. 20 min after injection—urine output was essentially the same as that observed during the control period. Doses approaching maximal response had the effect of gradually decreasing arterial blood pressure so that the blood pressure values observed at the end of the assay were 10–30 mm Hg lower than values observed prior to the injection of the extracts.

Figure 4:
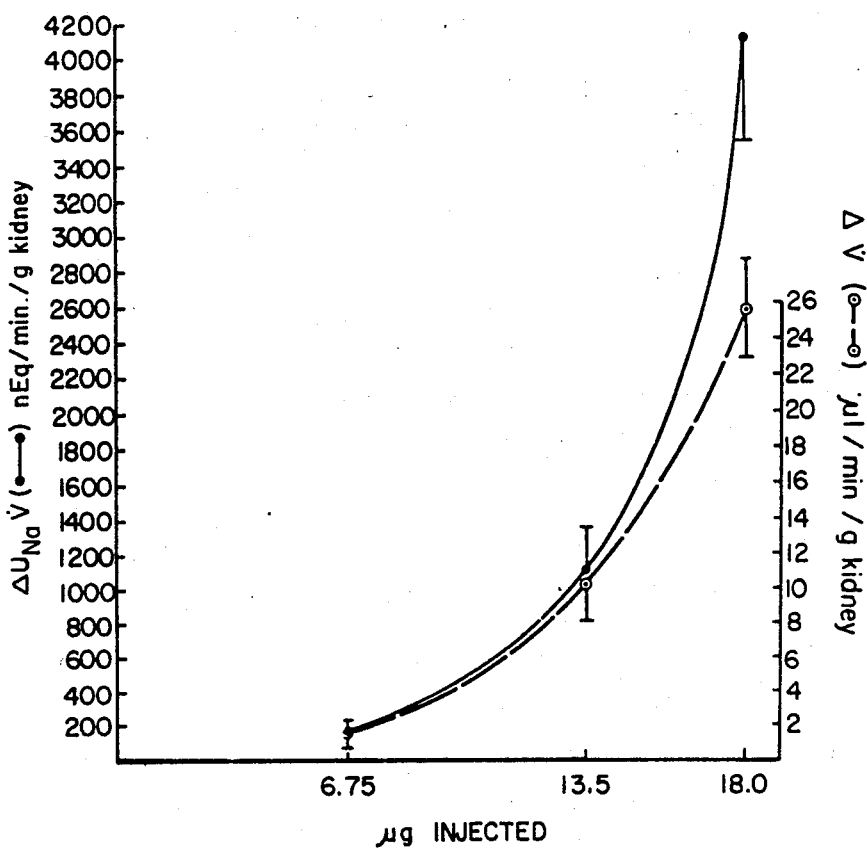
FIG. 4 is a graph illustrating net natriuretic and diuretic effect of partially purified natriuretic factor injected in a total volume of 0.2 ml of PBS. Net values were obtained by substracting total sodium excretions and urine output of animals injected with PBS alone from corresponding values of animals injected with natriuretic factor. (Values ±S.E.M.)

Both diuretic and natriuretic responses were dose dependent (FIG. 4). Maximal response obtained after injection of 18 µg of partially purified factor corresponded to a 30–40 fold and 10–15 fold increase in total sodium excretion and urine volume respectively.

Incubation of partially purified natriuretic factor with protease is illustrated in Table I overleaf, and shows completely abolished activity while samples incubated with inactivated enzyme had activities comparable to that of samples incubated with buffer alone. Protease digestion was carried out by incubating approximately 50 µg of partially purified natriuretic factor with 0.1 U of protease for 4 h at 37° C. in a total volume of 1.1 ml of 0.05M TRIS buffer, pH 7.6 (Group B). Controls were incubated with either boiled protease (Group C) or with buffer alone (Group A). (All values ±S.E.M.)

TABLE I

| | Group | Urine Volume µL/Min/G kidney | Total Excretions (nEq/min/g kidney) | | |
|---|---|---|---|---|---|
| | | | $Na^+$ | $K^+$ | $Cl^-$ |
| Bioassay | A (N = 6) | 2.39 ± 0.49 | 117 ± 27 | 643 ± 137 | 573 ± 158 |
| Control | B (N = 4) | 2.03 ± 0.84 | 68 ± 6 | 316 ± 52 | 151 ± 46 |
| Period | C (N = 4) | 2.14 ± 0.73 | 102 ± 39 | 578 ± 221 | 819 ± 250 |

TABLE I-continued

| Group | | Urine Volume μL/Min/G kidney | Total Excretions (nEq/min/g kidney) | | |
|---|---|---|---|---|---|
| | | | Na$^+$ | K$^+$ | Cl$^-$ |
| Bioassay | A (N.F.) | 13.20 ± 3.24* | 1074 ± 208* | 1902 ± 513† | 2850 ± 779* |
| Test | B (N.F. + Enz.) | 2.86 ± 1.09† | 71 ± 12† | 463 ± 181† | 383 ± 235† |
| Period | C (N.F. + Boiled Enz.) | 14.68 ± 2.36** | 1434 ± 190** | 1460 ± 96* | 2549 ± 343* |

Figure 5:
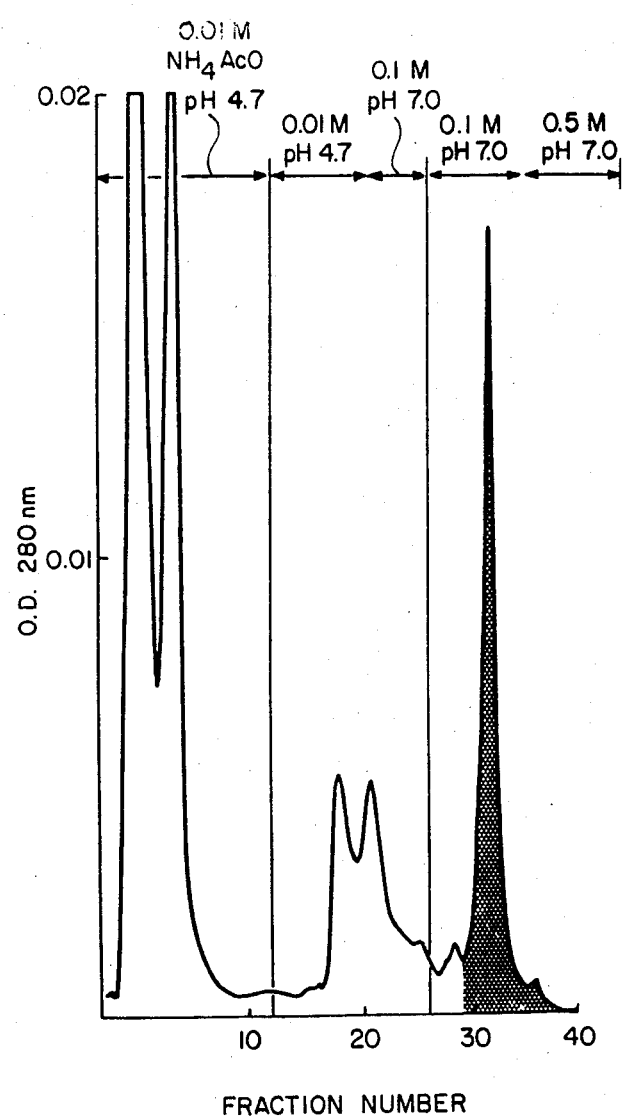
FIG. 5 is a bar graph illustrating ion exchange chromatography purification of partially purified natriuretic factor. Hatched area indicates fractions where natriuretic activity is recovered.

*, **Significant differences ($p < 0.05$, $p < 0.01$)
† No significant differences from control values Natriuretic factor distribution during chromatography in Sephadex ® G-75 (FIG. 2) was consistently multimodal although most of the activity was recovered in peaks corresponding to molecular weights of less than 6,000 Daltons. Further purification of this fraction was accomplished by ion exchange chromatography in CM Bio-Gel ® (FIG. 5) after which natriuretic activity was recovered in a single, though not symmetrical, peak.

The fact that natriuretic activity is recovered after desalting in a Bio-Gel ® P-2 column (normal fractionation range: 100-1,800 Daltons) is of considerable interest because it shows that natriuretic factor is distinct from inorganic salts and low molecular weight organic compounds which are likely extracted by acetic acid and which may be expected to be cardioactive and/or affect kidney function.

The significance of multimodal distribution of natriuretic factor after chromatography in Sephadex ® G-75 is not clear. Protein interaction, possibly including polymerization, appears as the most likely explanation.

Protease sensitivity as well as the general behaviour of natriuretic factor suggest that it is a polypeptide.

The second technique for extraction of ANF follows a general outline for the isolation and purification of pituitary peptides described by Bennett et al "Purification of the Two Major Forms of Rat Pituitary Corticotrophin Using Only Reverse-Phase Liquid Chromatography" Biochemistry, 20: 4530-4558, (1981). Heart tissues are homogenized in an aqueous extractant mixture typically containing 1.0M acetic acid, 1% sodium chloride and 1.0M hydrochloric acid. Other organic acids, mineral acids or salts may, of course, also be used. The extracts are then treated with octadecylsilyl silica in a batch procedure and ANF is further purified using reverse phase high performance liquid chromatography.

EXAMPLE 4

Rat atria, freshly dissected and frozen, were obtained commercially. The frozen tissue was finely ground and an acetone powder prepared by repeated extraction with acetone and hexane. Up to 700 mg of the dried powder was extracted three times with 20, 10 and 10 mL respectively of an aqueous extractant consisting of 1.0M acetic acid, 1.0M hydrochloric acid and 1% sodium chloride. Extraction was carried out on ice using a ground-glass homogenizer. The extracts so obtained were centrifuged and the supernatant was passed through two octadecylsilyl silica (ODS-silica) cartridges ($C_{18}$ Sep-Pak ®, Waters Associates). Before use, the cartridges were wetted with 5 ml of 80% acetonitrile (ACN)/water containing 0.1% trifluoroacetic acid (TFA) and rinsed with 5 ml of 0.1% TFA. After passing the samples, the cartridges were rinsed with 20 ml of 0.1% TFA. Compounds bound to the cartridges (including artrial natriuretic factor) were eluted by passing 3 ml of 80% ACN/0.1% TFA. The eluate from each cartridge was diluted to 18 mL with 0.1% TFA and pumped through the "aqueous" pump of a high performance liquid chromatograph for binding to a μ-Bondapak ® $C_{18}$ chromatographic column (Waters Associates) previously equilibrated with 12% ACN/0.1% TFA. The column was then eluted using a gradient of 20 to 40% ACN. Two active fractions are recovered. These fractions were further purified by separate re-chromatography in the same system this time using ACn gradients containing 0.1% heptafluorobutyric acid (HFBA). Active fractions from HFBA gradients were purified once more by another gradient chromatography using TFA-containing ACN gradients. Injection of test samples of the extract thus produced into non-diuretic rats according to the procedure outlined in Example 3 resulted in similar results to those described in Example 3.

EXAMPLE 5

Figure 6:
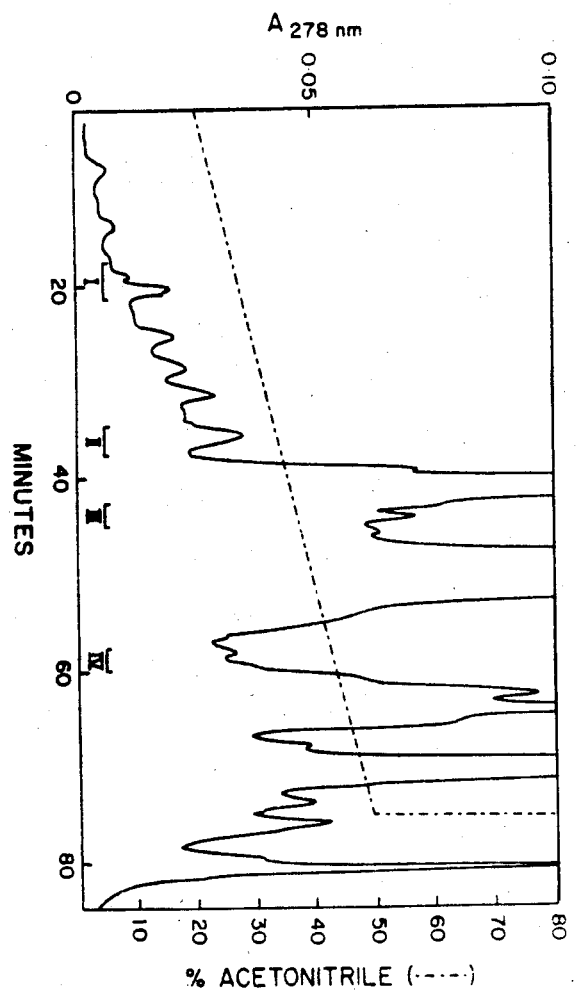
FIG. 6 is an RP-HPLC elution profile of an acid extract of rat atrial muscle.
Figure 7:
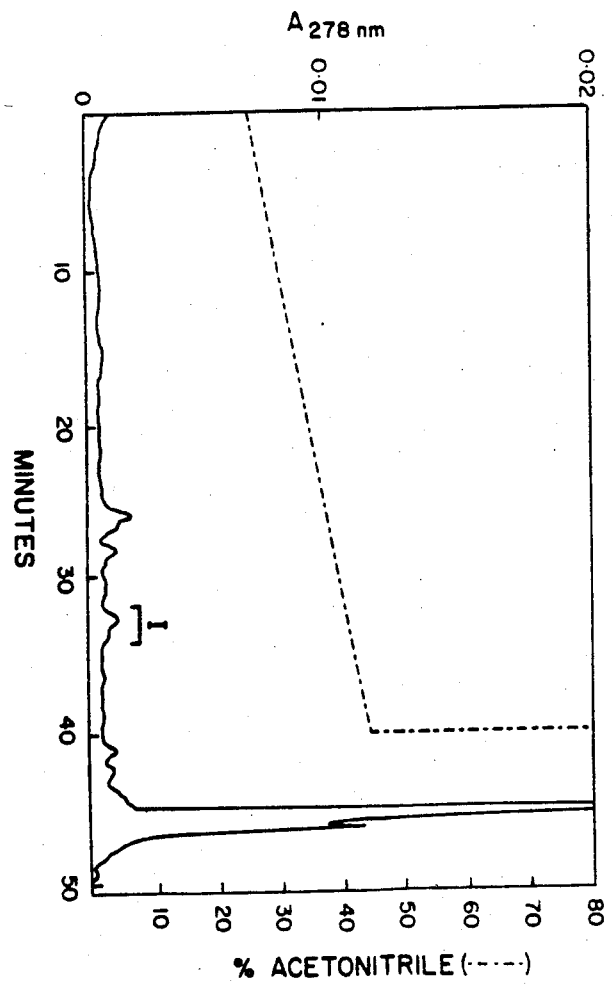
FIG. 7 is an RP-HPLC elution profile of region I of FIG. 6, after chromatography in HFBA-containing $CH_3CN$ gradient.
Figure 8A:
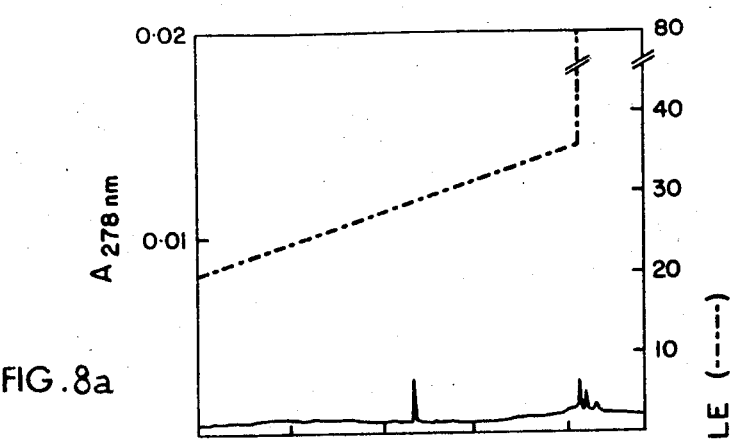
FIGS. 8a and 8b are RP-HPLC elution profiles obtained after rechromatography in a TFA-containing $CH_3CN$ gradient of active material from chromatography using HFBA (FIG. 7)
Figure 8B:
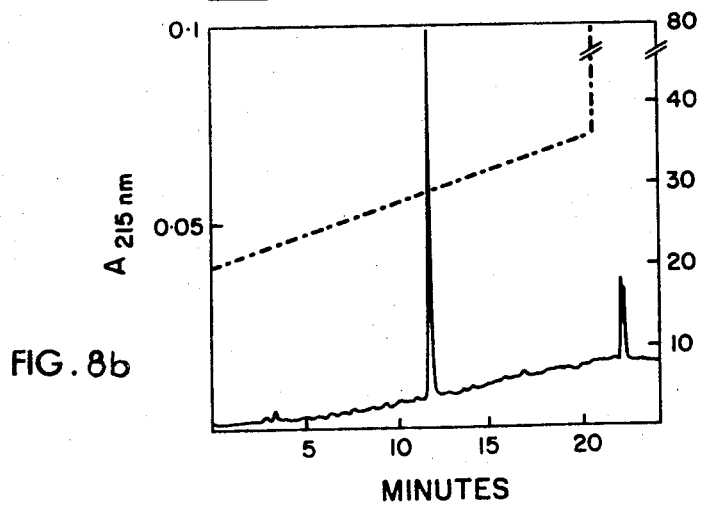

Atria were obtained from adult male Sprague-Dawley rats. The tissues were kept frozen ($-70°$ C.) from 24 to 72 h before being pulverized in a household-type coffee grinder previously cooled by grinding dry ice chips. The frozen tissue powder was then poured into a beaker containing 10 volumes of an ice-cold aqueous extractant composed of 1.0M acetic acid, 1.0N HCL and 1% NaCl and homogenized using a Polytron fitted with a PT35 probe operated for 60 s at 50% power The homogenate was stirred for 1 h in the cold before centrifuging. The pellets thus obtained were re-extracted following an identical protocol but using 5 volumes of the extractant. The supernatants from the two extractions were combined and 40 ml aliquots were passed five times through Sep-Pak cartridges (Waters) which were then washed with 20 ml of 0.1% trifluoroacetic acid (TFA) and eluted with 3 ml of 80% acetonitrile ($CH_3CN$) in 0.1% TFA. The eluates were then diluted with 0.1% TFA in a proportion of 15 ml of acid to 3 ml of cartridge eluate. The diluted eluate was pumped into a HPLC column (μ-Bondapak $C_{18}$, 7.8×300 mm) through the "B" (aqueous) pump of a series 2/2 Perkin-Elmer liquid chromatograph. The column had previously been equilibrated with 12% $CH_3CN$ in 0.1% TFA and gradient elution was carried out over 75 min at 1.5 ml/min with a linear gradient of 20–50% $CH_3CN$ in 0.1% TFA. Column effluent was monitored at 278 nm (LC55 Perkin-Elmer detector) and collected in 2 min fractions. Aliquots of the fractions were freeze-dried and re-suspended in phosphate-buffered saline (PBS) for natriuretic factor assay. FIG. 6 shows the elution profile of extracts obtained from 200 atria after RP-HPLC. The extract obtained from 200 rat atria was pumped directly into the chromatographic column (μ-Bondapak $C_{18}$, 7.8×300 mm) and eluted over 75 min with a gradient of 20–50% $CH_3CN$ in 0.1% TFA. Two min fractions were collected. Aliquots of these fractions were freeze-dried and re-suspended in PBS for assay of natriuretic activity. Activity was found distributed in four discrete regions of the chromatogram. The fractions comprising region I were pooled, diluted 1:1 with aqueous 0.13% heptafluorobutyric acid (HFBA) and pumped back into the column which had been equilibrated with 12% CH$_3$CN in 0.13% HBFA. Elution of the column was carried out over 40 min with a gradient of 28-44% CH$_3$CN in 0.13% HFBA. Activity was recovered in fractions eluting between 31 and 34 min (FIG. 7). These fractions were diluted 1:1 with 0.1% aqueous TFA and re-chromatographed using a 3.9×300 mm μ-Bondapak C$_{18}$ column eluted over 20 min with a gradient of 20-36% CH$_3$CN in 0.1% TFA. As shown in FIG. 8, a sharp, symmetrical peak was now obtained which was apparently homogeneous at both 278 nm (FIG. 8a) and 215 nm (FIG. 8b).

The product obtained at this point was referred to as "cardionatrin I". Total yield of cardionatrin I varied from 12-20 nmol per 1,000 atria. The material obtained from 200 rat atria was used to obtain a molecular weight estimate using urea-sodium dodecylsulfate-polyacrylamide gel electrophoresis (SDS-PAGE).

Further characterization studies on "cardionatrin I" have been carried out using preparations of cardionatrin I derived from 1,000 rat atria, as follows: amino acid analysis after hydrolysis in 6N HCL both with or without prior performic acid oxidation; amino acid analysis after hydrolysis in 4N methanesulfonic acid; spectrophotometric determination of tryptophan.

Figure 9:
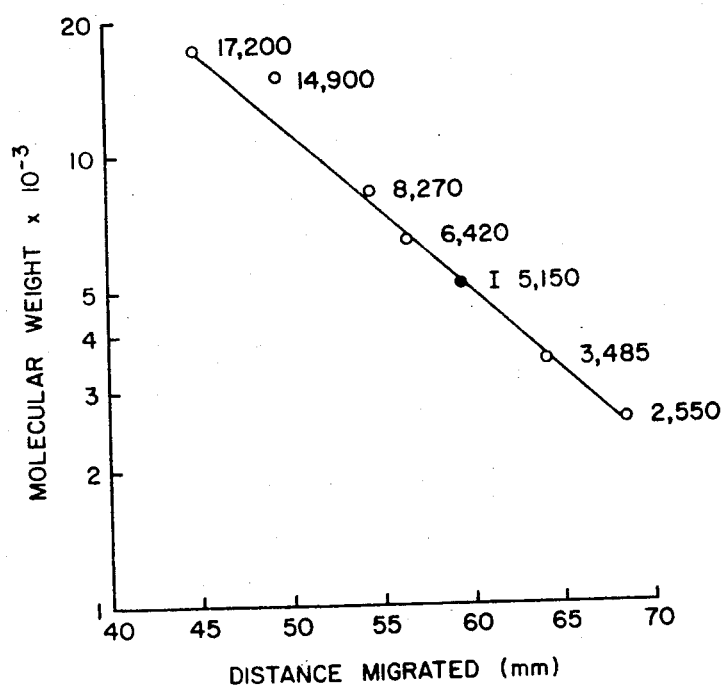
FIG. 9 is a graph of molecular weight versus migrated distance for SDS-Page comparison.

The molecular weight of cardionatrin I was estimated by SDS-PAGE. Cardionatrin I (I) obtained from a 200-rat atrial extract, was analyzed by urea SDS-PAGE together with molecular weight standards. The standards were cyanogen bromide fragments of sperm whale myoglobin (MF) and commercially obtained glucagon (G). Plot of molecular weight versus migrated distance (FIG. 9) gives an estimate of 5,150 for the molecular weight of cardionatrin I (I).

Amino acid analysis (Table II)

TABLE II

Figure 10:
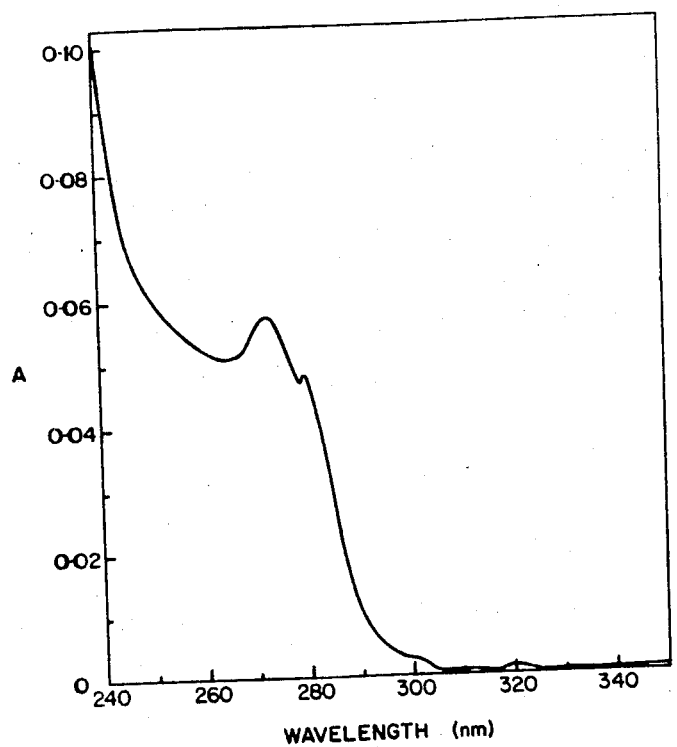
FIG. 10 is a UV absorption spectrum of cardionatrin I.

| Amino Acid Composition of Cardionatrin I | |
|---|---|
| Amino Acid | No. of Residues |
| Asp | 3.7 (4) |
| Thr | 1.3 (1) |
| Ser | 6.4 (6) |
| Glx | 4.8 (5) |
| Pro | 1.9 (2) |
| Gly | 7.3 (7) |
| Ala | 3.3 (3) |
| Cys | 0.9 (1) |
| Val | 1.0 (1) |
| Met | 0.8 (1) |
| Leu | 3.2 (3) |
| Tyr | 1.1 (1) |
| Phe | 1.8 (2) |
| Lys | 2.8 (3) |
| His | 1.1 (1) |
| Trp | 0.0 (0) |
| Arg | 5.7 (6) |
| Total no. of residues | 47 | revealed that the peptide consisted of 47 residues one of which was cystine, indicating that cardionatrin I contains a disulfide bond. No tryptophan residue was detected by amino acid analysis following hydrolysis of the peptide in 4N methanesulfonic acid. The UV spectrum of the peptide also did not show the shoulder at 288 nm characteristic of tryptophan containing peptides (FIG. 10). The spectrum was obtained using a Cary 210 spectrophotometer with a 10 mm light path and equipped with automatic baseline adjust. For the spectrum shown, 10 nmol of cardionatrin I were dissolved in 1.0 mL of 0.1N HCL. The molecular weight of cardionatrin I estimated from the amino acid composition was 5273 which is in close agreement with that estimated by SDS-PAGE gel electrophoresis.

Injection of 0.5 nmol of purified cardionatrin I induced a characteristic diuretic response of rapid onset and decay in the non-diuretic bioassay rat, resulting in a two-fold increase in urine output and a four-fold increase in sodium excretion. From previous dose-response studies using partially purified preparations, maximal bioassay response for cardionatrin I may be expected to be in the 1 to 2 nmol range.

The ability of either crude atrial extracts or partially purified atrial natriuretic factor to induce a rapid and potent diurectic and natriuretic response in bioassay animals has been noted above. In addition, recent tissue fractionation studies, have shown that this activity appears largely stored in the secretory-like specific atrial granules. These granules share histochemical and tinctorial properties with granules known to store polypeptide hormones. Histochemical data suggest the presence of sulphur-containing amino acids in atrial granules and cardionatrin I contains a cystine residue and a methionine residue. However, the histochemical studies also indicate the presence of indole in atrial granules, but the amino acid composition of cardionatrin I showed that no tryptophan was present. The reasons for this apparent discrepancy are not clear at present but could be related to the specificity of the histochemical technique or the presence of other indole containing species within atrial granules. Clarification of this may be expected with the characterization of the remaining peptides with natriuretic activity found after RP-HPLC of atrial homogenates.

The ANF of the present invention is clearly a highly useful pharmaceutical composition for diuretic and natriuretic purposes and is also believed to be of great potential in reaching a better understanding of the in vivo control of water and electrolyte balance. Should future investigations show that peptides such as cardionatrin I are released from the atria to modify kidney function then this would have a major impact on the understanding of disturbances of water and electrolyte balance which occur in such clinical entities as essential hypertension and chronic congestive heart failure.

I claim:

1. In the process for extracting a fraction containing a diuretic and natriuretic factor from rat heart atria, which contain the factor, by excising the hearts, homogenizing in a homogenizer and separating the active factor, the improvement for producing said factor in a purified form comprising:
   (a) homogenizing frozen rat heart atria in an aqueous solution of 1.0M acetic acid to thereby extract said factor into said solution;
   (b) adjusting the pH of said solution to within the range of 4.5 to 7.6 to thereby precipitate proteinaceous impurities from the solution containing the factor and removing the impurities from the solution;
   (c) reducing the volume of the solution by freeze drying; and
   (d) chromatographically treating said solution at least once by passage through a column containing an ion exchange agent to separate and to purify a fraction containing said diuretic and natriuretic factor and recovering said fraction, said fraction containing a peptide having diuretic and natriuretic properties.

2. A process as claimed in claim 1 wherein said ion exchange chromatography step (c) comprises passage of the solution through an ion exchange column which has been equilibrated with 1.0M acetic acid and thereafter pooling active fractions and freeze drying the fractions.

* * * * *